United States Patent [19]

Jones et al.

[11] E Patent Number: Re. 33,088

[45] Reissued Date of Patent: Oct. 10, 1989

[54] METHOD AND APPARATUS FOR RECORDING MEDICAL INFORMATION ON A STRIP CHART

[75] Inventors: Flave L. Jones, Guilford; Mark L. Kelly, Middletown, both of Conn.

[73] Assignee: American Home Products Corporation, New York, N.Y.

[21] Appl. No.: 889,319

[22] Filed: Jul. 23, 1986

Related U.S. Patent Documents

Reissue of:

[64] Patent No.: 4,513,295
Issued: Apr. 23, 1985
Appl. No.: 544,325
Filed: Oct. 21, 1983

[51] Int. Cl.[4] ..... G01D 9/00; A61B 5/04

[52] U.S. Cl. ..... 346/1.1; 346/33 ME; 128/630; 128/698; 364/413.03; 364/413.02

[58] Field of Search ..... 346/33 ME, 1.1; 128/630, 698, 731, 733; 364/413, 415, 416

[56] References Cited

U.S. PATENT DOCUMENTS

| | | | |
|---|---|---|---|
| 3,977,394 | 8/1976 | Jones et al. | 364/415 X |
| 3,989,034 | 11/1976 | Hojaiban | 128/698 |
| 4,033,336 | 7/1977 | Murawski et al. | 346/33 ME X |
| 4,051,522 | 9/1977 | Healy et al. | 346/33 ME X |
| 4,090,505 | 5/1978 | Mortara | 346/33 ME X |
| 4,219,028 | 8/1980 | Lencioni, Jr. | 128/731 |
| 4,299,234 | 11/1981 | Epstein et al. | 128/698 |
| 4,331,962 | 5/1982 | Neumann | 346/33 ME |

OTHER PUBLICATIONS

Adaniya, G., "Keyboards—Control/Display Units", Medical Electronics, Feb., 1980, pp. 69–73.

FETA SCAN 1000 Obstetrical Data System (Imager Display/Fetal Monitor), Cranbury Medical Labs, 102C00002-01B, 1982.

CML Introduces Feta Scan Line, SCANNER, vol. III, No. 11, May 28, 1982, pp. 2–3.

FETASCAN 1000 Operation Manual, 105C00001-01, Jun. 1982.

Hewlett Packard, Fetal Monitoring Data 80220A Patient Data Memory System, 6/79.

Burdick's M565 Color-Trend Monitor, The Burdick Corporation, Milton, Wis. 53563.

*Primary Examiner*—George H. Miller, Jr.
*Attorney, Agent, or Firm*—Darby & Darby

[57] ABSTRACT

For recording medical information on a strip chart by a strip chart recorder associated with a fetal monitoring device, a communication is initially entered into a data entry system which includes a switching membrane having a plurality of switches forming a switching network underlying the membrane. A microprocessor scans the network to identify the communication and thereafter supplies the same to a liquid crystal display for view by a user of the system prior to transmission of the communication to the recorder for recordation.

33 Claims, 5 Drawing Sheets

METHOD AND APPARATUS FOR RECORDING MEDICAL INFORMATION ON A STRIP CHART

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to the recording of medical information by a strip chart recorder and, more particularly, is directed toward a method *and apparatus* for recording medical information by a strip chart recorder in which the information is initially communicated to a data entry system.

2. Description of the Prior Art

For graphically recording fetal heart rate (FHR) and uterine activity (UA) measured by a fetal monitoring device, a strip chart recorder, having a two-channel strip chart is typically employed. Additional information which may be of interest, such as time of day, paper speed and FHR and UA monitoring modes, is recorded by the recorder between the two channels of the strip chart. An apparatus presently available which incorporates the above is the Hewlett Packard Model 8040A Fetal Monitor.

Recorders, such as incorporated in the Model 8040A, however, unduly limit the variety of information available for documentation by the recorder. More particularly, the recorders are unable to record information which may be highly pertinent in interpreting the graphs of FHR and UA. For example, it may be extremely important to know whether the mother has changed positions while being monitored, whether medication is being administered, the fetal pH levels and temperature of the mother, the oxygen, intravenous and oxytocin rates being administered to the mother, and the maternal pulse, respiration, and blood pressure.

Up to now, such pertinent information has had to be jotted down by a nurse or doctor on the strip chart by non-automatic means, that is, by hand while the strip chart was moving due to advancement of the chart by the recorder. Consequently, the pertinent information was, at times, illegible. Furthermore, by being forced to record the pertinent information by hand, the doctor or nurse had to walk over to the recorder and away from the mother which could be extremely inconvenient, if not impossible, because of the physical location of the recorder and/or condition of the mother.

Of course, some of this pertinent information may not be always applicable or need be recorded only when a change in the particular parameter of information has occurred. For example, if the ph level remains constant there is no need to record the ph level over and over on the strip chart. Thus, the doctor or nurse should be free to pick and choose when and which parameters of pertinent information are to be recorded by the recorder on the strip chart.

OBJECTS AND SUMMARY OF THE INVENTION

Consequently, it is an object of the present invention to provide a method *and apparatus* by which a strip chart recorder prints medical information on a strip chart which avoids the above described prior art drawbacks.

More specifically, it is an object of the present invention to provide a new and improved method [of] *and apparatus for* recording medical information on a strip chart by a strip chart recorder which substantially increases the amount of medical information available for recordation by the recorder and which thereby substantially eliminates the need to record such information by hand.

It is another object of the present invention to provide a method [of] *and apparatus for* recording medical information on a strip chart by a strip chart recorder which provides selectivity in the information to be recorded.

In accordance with an aspect of this invention, for printing by a strip chart recorder and displaying by a display device medical information, a method comprises communicating medical information to switching membrane means; scanning said switching membrane means; generating one of a plurality of membrane signals in response to each communication and scan; identifying said one of said plurality of membrane signals; displaying said medical information in response to said identification; and printing said medical information in response to said identification *after said medical information has been displayed.*

In communicating said medical information to said membrane switching means, it is a feature of the present invention that said switching membrane means comprise a plurality of depressible keys overlying a corresponding plurality of switches wherein at least one of said keys is depressed in order to effect said communication.

In accordance with another feature of the present invention, the medical information is selected from the group of functions consisting of pH, temperature, intravenous rate, oxygen rate, pulse, respiration, blood pressure, oxytocin rate, effacement, dilation, fetal station, maternal position change, rupture of membrane, medication, fetal movement and vaginal exam and from numerical data and symbols associated therewith.

The above, and other objects, features and advantages of this invention will become apparent from the following detailed description which is to be read in conjunction with the accompanying drawings.

DETAILED DESCRIPTION OF A PREFERRED EMBODIMENT

Figure 1:
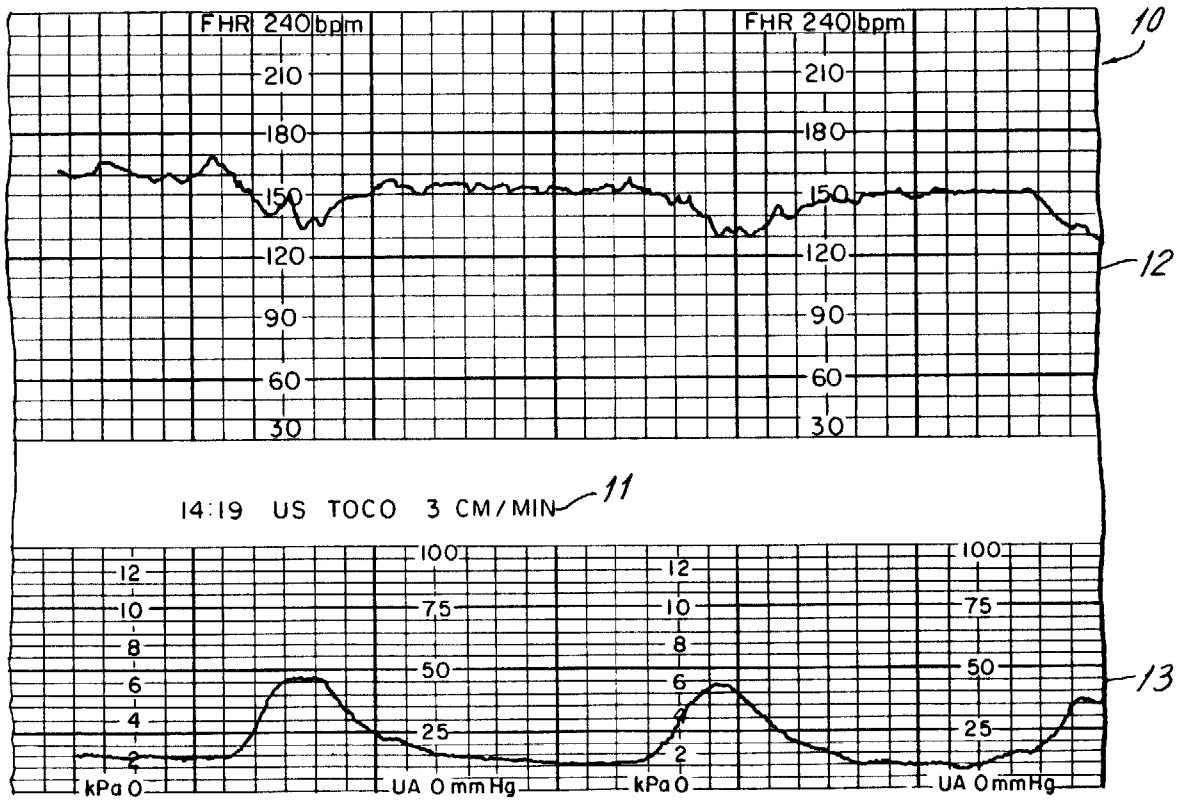
FIG. 1 PRIOR ART
FIG. 1 illustrates graphical representations of fetal heart rate and uterine activity and typical prior art annotations documented by a recorder on a strip chart.

Referring now to FIG. 1, a two channel strip chart, 10, of a strip chart recorder is shown which graphically documents fetal heart rate (FHR) and maternal uterine activity (UA) detected by a fetal monitoring device (not shown). Information such as time of day, paper speed, and modes in which the fetal heart and uterine activity are monitored are automatically annotated in area 11, which is located between the FHR and UA channels as represented by graphs 12 and 13, respectively.

Additional information, however, such as maternal pulse rate, blood pressure, respiration, etc. must be entered on strip chart 10 by non-automatic means, that is, by hand. Thus a nurse or doctor, who is notorious for illegibility, is forced to enter pertinent information associated with the aforementioned graphic representations by hand. Besides the additional information frequently being illegible, the doctor or nurse must walk away from the mother and over to the recorder in order to document such additional information which can be extremely inconvenient, if not impossible, due to the physical location of the recorder and/or the condition of the mother. Additionally, inasmuch as a great deal of medical information may be required to be annotated on the strip chart, it may be difficult to record the same thereon without overlapping onto the FHR and/or UA channels resulting in further illegibility.

Figure 2:
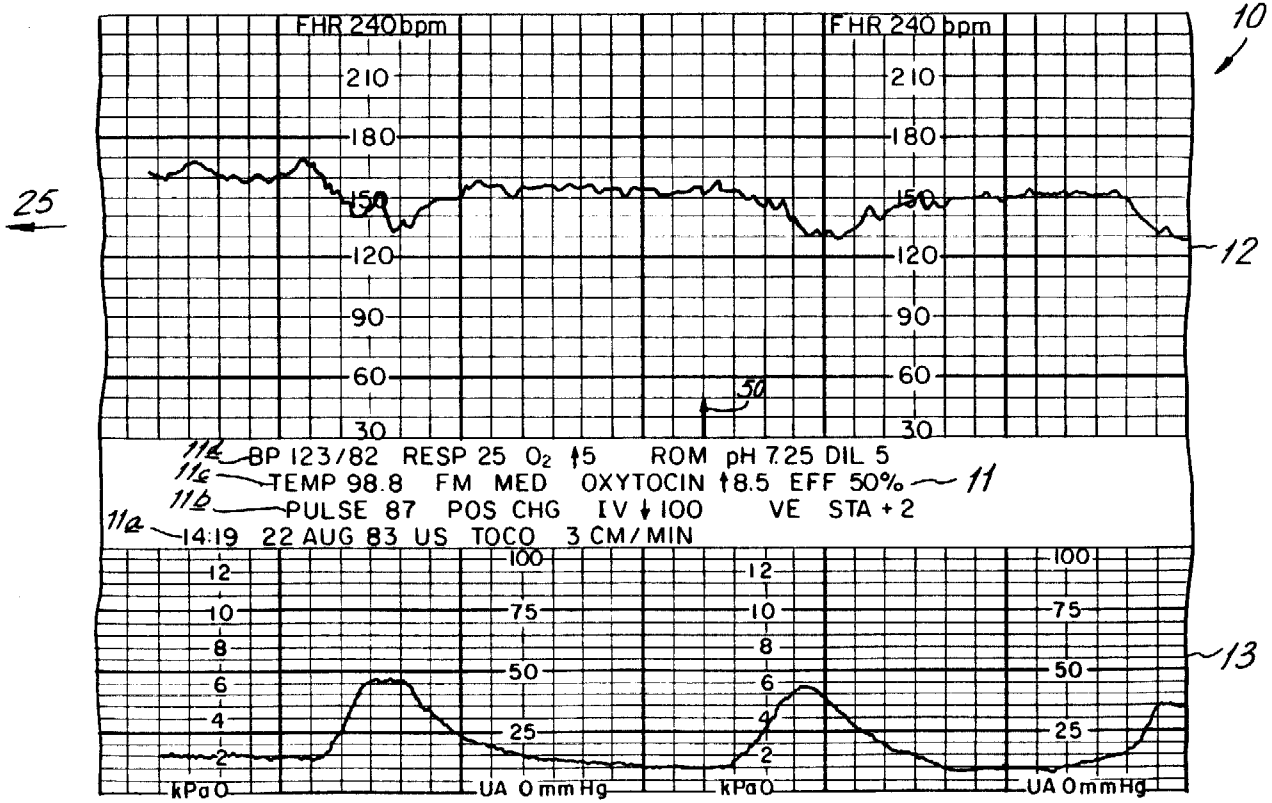
FIG. 2 illustrates graphical representations of a fetal heart rate and uterine activity and various annotations documented by a recorder on strip chart in accordance with an embodiment of the present invention.

In accordance with an embodiment of the present invention, FIG. 2 illustrates the variety of annotations which can be printed by a strip chart recorder in area 11 of strip chart 10, More specifically, information documented by a recorder 20, as supplied from a fetal monitoring device 21, includes the automatic annotations of time of day, date, monitoring modes of both the FHR and UA and strip chart speed. Other information, hereinafter referred to as functions, communicated to a data entry system 30 (to be discussed below) and which is documented by recorder 20, includes maternal pulse rate, position change of mother, intravenous rate, fetal pH level, maternal temperature, oxygen rate, respiration, blood pressure, oxytocin rate, effacement, size of dilation, fetal station, rupture of membrane, whether medication is being administered and whether a vaginal examination is being made. Obviously, such a plethora of information would be difficult to record in a legible format by hand and within area 11 so as not to interfere with or overlap the FHR or UA graphs 12 and 13, respectively.

Area 11 can accommodate four lines of information. Line 11a, which normally is reserved for the previously-mentioned automatic annotations, shows a time of day of 1419 hours (i.e. 2:19 p.m.) on Aug. 22, 1983, an external FHR monitoring mode employing ultrasound (US), an external UA monitoring mode employing a tocodynamometer (TOCO) and a strip chart speed of 3 cm/minute. Other FHR monitoring modes, (to be explained below), which can be recorded on line 11a, include phono (PHONO) and fetal ECG (FECG). Other UA monitoring modes (to be explained below), which can be recorded on line 11a, include an intrauterine catheter and strain gauge denoted as intrauterine pressure (IUP). Lines 11b, 11c and 11d are reserved for additional information communicated through data entry system 30. For illustrative purposes only, line 11b shows the maternal pulse to be 87 beats per minute (PULSE 87), that the mother has changed positions (POS CHG), that the intravenous rate in units of, for example, cc/hr. or drops/min, has dropped by 100 (IV ↓ 100), that a vaginal exam (VE) is being conducted and that the fetus has dropped to station +2 (STA+2). Line 11c shows that the temperature of the mother is 98.8° F. (TEMP 98.8), that fetal movement (FM) is occurring and that medication is being administered (MED), that the oxytocin rate in, for example, milliunits/min. or drops/min. has been increased to 8.5 (OXYTOCIN ↑ 8.5) and the effacement to be at 50% (EFF 50%). Line 11d includes a blood pressure reading of 123/82 (BP 123/82), respiration rate of 25 breadths/minute (RESP 25), an increase in the rate of oxygen administered to 5 liters/min. ($O_2$ ↑ 5), a rupture of the membrane (ROM), a fetal pH reading of 7.25 (pH 7.25) and dilation of 5 (DIL 5). Of course, not all of the additional information shown on lines 11b, 11c and 11d need be documented. Additionally, the order in which the information appears on lines 11b, 11c and 11d is dependent entirely on the sequential order in which the information is communicated to data entry system 30. Furthermore, as is readily apparent, the entries on lines 11b, 11c and 11d are staggered relative to each other due to advancement of strip chart 10 by recorder 20 in the direction of arrow 25.

Figure 3:
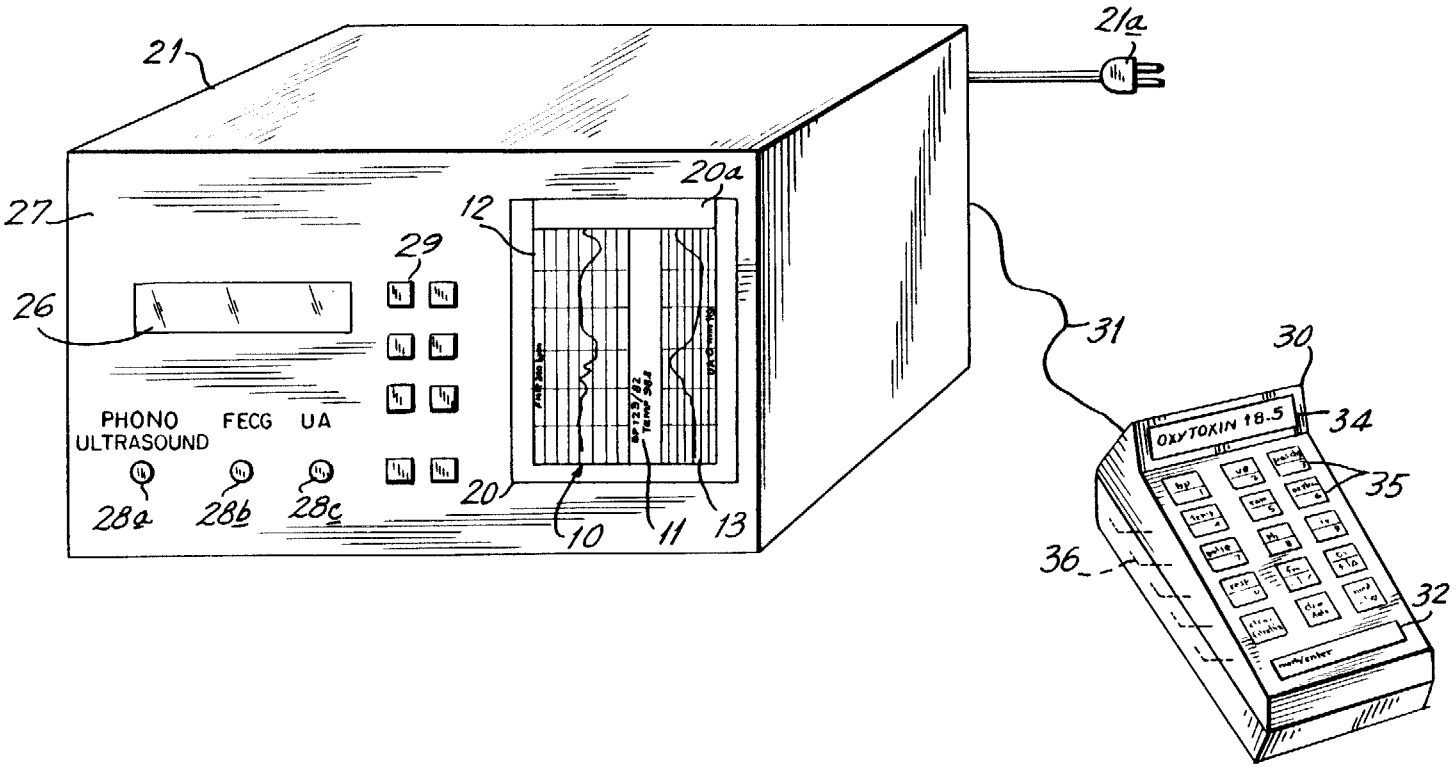
FIG. 3 is a perspective view of a fetal monitoring system which includes a strip chart recorder for recording medical information as shown in FIG. 2 and a data entry system for entering medical information which is to be documented by the recorder on the strip chart in accordance with an embodiment of the present invention.

Referring now to FIG. 3, fetal monitoring device 21 monitors both fetal heart rate and maternal uterine contractions. Simultaneous trends of beat-to-beat FHR and UA are plotted continuously on strip chart 10 by a thermal printhead 20a of strip chart recorder 20. A thermal printhead suitable for use with the present invention is manufactured by Ricoh Systems, Inc. and identified as Model TH3650. Additionally, the FHR is displayed continuously on a front-panel numeric display, such as light emitting diodes 26. Fetal monitoring device 21 monitors and determines FHR and UA using the following external or internal clinical methods:

For determining FHR, external monitoring modes include ultrasound (US) and phono. More particularly, in connection with US, ultrasound transducers placed on the abdomen direct an ultrasonic beam toward the fetal heart and sense Doppler-shifted echoes created by moving cardiac structures whereas in connection with phono, acoustically sensitive transducers are placed on the abdomen for sensing fetal heart sounds. For internally monitoring FHR, a method commonly employed in the art, comprises attaching a spiral electrode to a fetal presenting part and computing FHR on a beat-by-beat basis using the time interval between R-wave peaks. Such a monitoring mode is commonly referred to as direct fetal ECG (FECG). Readings of the fetal heart rate are shown graphically in beats per minute whether using an external or internal monitoring mode.

For determining UA, an external monitoring mode employs a tocodynamometer (TOCO). The tocodynamometer measures relative tension of the maternal abdominal wall in response to changes in pressure within the uterus by using a tocotransducer strapped to the abdomen in the area of uterine fundus. The tocodynamometer readings are plotted on a relative scale of 0 to 100. An internal mode for monitoring uterine activity employs an intrauterine catheter and strain gauge wherein amniotic fluid pressure is measured using a transcervical intrauterine catheter and externally mounted strain gauge. In contrast to the tocodynamometer, pressure changes are plotted over a range of 0 to 100 mmHg.

Provided on front panel 27 of fetal monitoring device 21, is an input jack 28a for connection to an acoustic or ultrasound transducer and input jack 28b for connection to a spiral electrode for determining FHR. Similarly, an input jack 28c is provided for connection to a tocodynamometer or strain gauge for determining UA. Front panel controls 29 are provided for adjusting the volume of sound emitted by a rear panel speaker (not shown) and for setting the UA channel when using an intrauterine catheter and strain gauge or a tocodynamometer to monitor UA. Other controls initiate a self-test routine monitor, activate or deactivate recorder 20, turn device 21 on and off, cause an arrow-shaped mark to be printed on heart rate channel 12 of strip chart 10, and increase the rate of advancement of strip chart 10.

Electrical power is supplied to fetal monitoring device 21 from a power source (not shown) through a power cord 21a connected to the rear panel of device 21. Also connected to the rear panel of device 21 are a plurality of lines, shown as a conductor 31 which connects device 21 to data entry system 30. Power is supplied through one of these lines to data entry system 30. Furthermore, inasmuch as conductor 31 can be of any desired length, for example, approximately ten feet, a doctor or nurse need not be immediately adjacent to device 21 in order to operate data entry system 30. Thus in operating the present invention, there is no need to walk away from the mother.

Figure 4A:
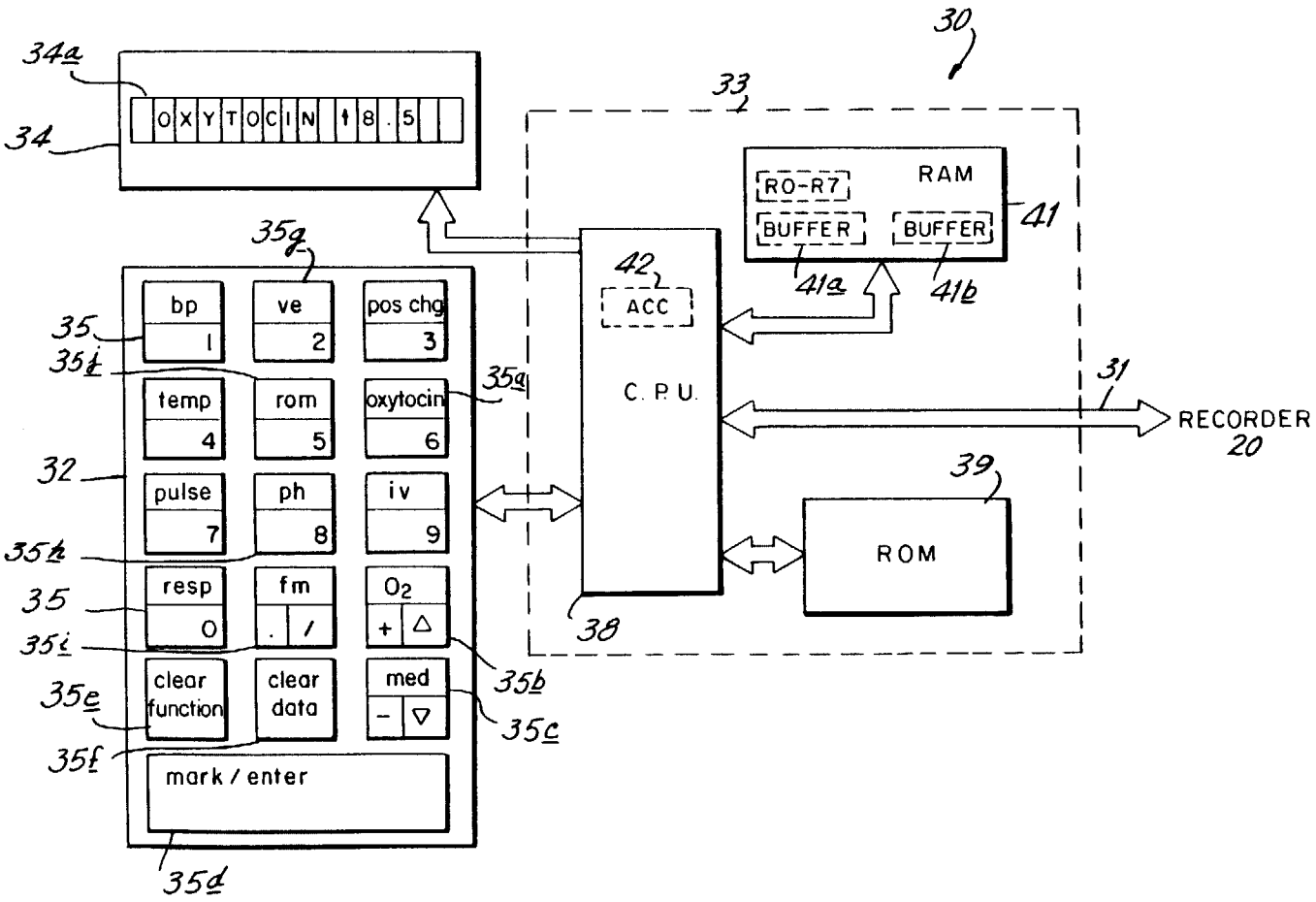
FIGS. 4A and 4B are a block diagram of the data entry system and a schematic diagram of the switching network included in the data entry system, respectively.

Data entry system 30, which resembles a hand-held electronic calculator, comprises a membrane switch 32, liquid crystal display 34 and microprocessor 33. Membrane switch 32 is a thin, soft, pliable sheet of plastic having a plurality of depressable keys 35 overlying a corresponding plurality of switches 36 forming a switching network 37 in the form of a 4×4 matrix. Each of the switches 36, which is a normally open, momentary contact switch, is switched to its respective conductive state by depressing the corresponding key. Switching network 37 is connected to microprocessor 33, which, for example, can be a single chip microprocessor, such as microprocessor chip no. 8749H manufactured by Intel Corporation. As shown in FIG. 4A, microprocessor 33 includes a central processing unit (CPU) 38, read-only-memory (ROM) 39 and random-access-memory (RAM) 41 wherein CPU 38 is connected to both ROM 39 and RAM 41. CPU 38 is also connected to display device 34. After microprocessor 33 processes the signal read from switches 36, the processed signal is supplied by microprocessor 33 to display 34. Consequently, the user, such as a nurse or doctor, of system 30 can view the medical information communicated to system 30 prior to printing of the same by recorder 20. Thus a mistake in communication to system 30 can be corrected prior to printing of the same by recorder 20. Display 34 also contains a microprocessor. Such a display is well known in the art as a "smart display" inasmuch as the display contains all of the electronics required to process and display an alphanumeric message based on a digital signal supplied by microprocessor 33.

Figure 4B:
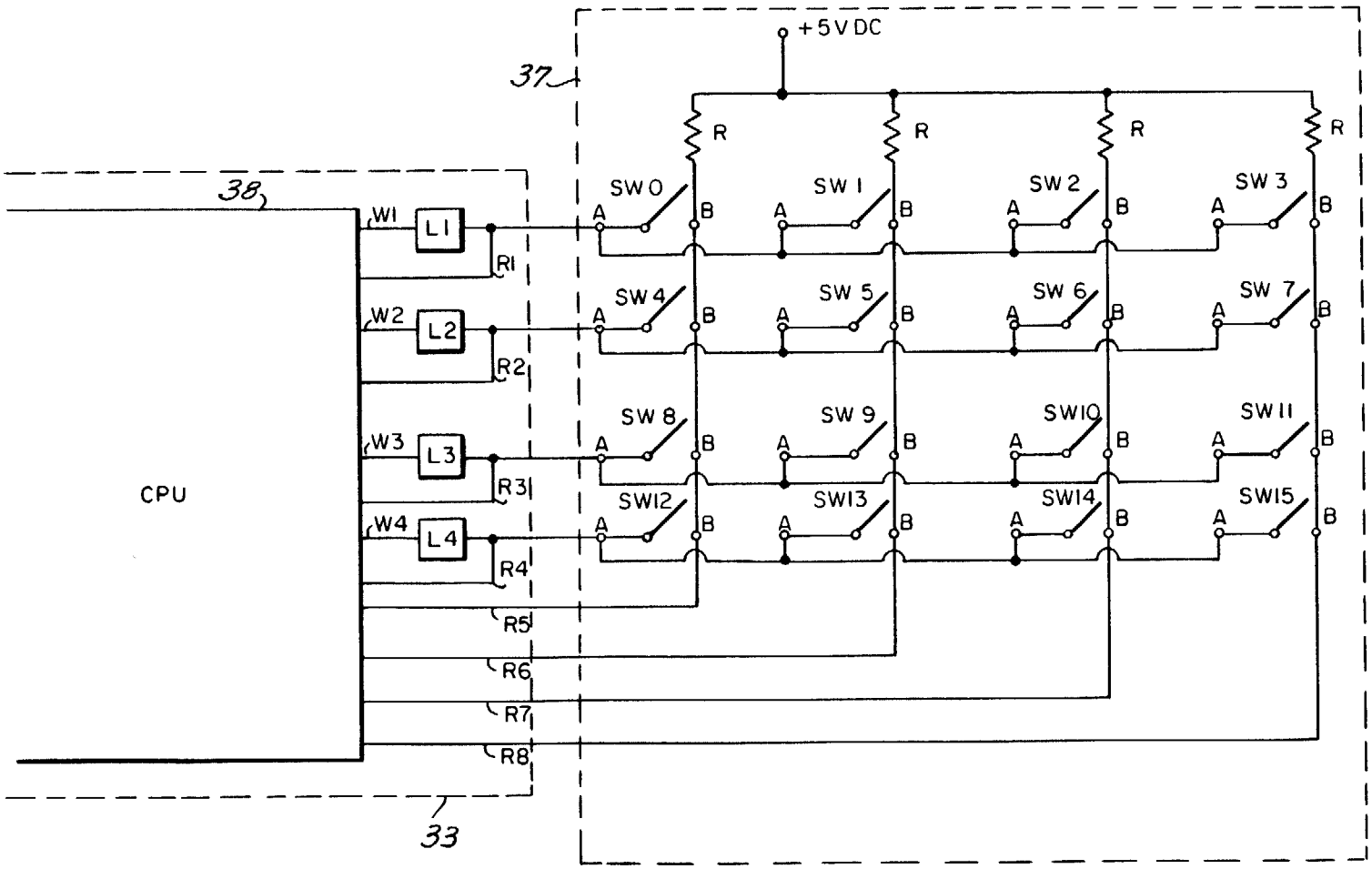

As shown in FIG. 4B, switching network 37 comprises switches SW0–SW15 forming four rows and four columns. Rows 1,2,3 and 4 include SW0, SW1, SW2 and SW3; SW4, SW5, SW6 and SW7; SW8, SW9, SW10 and SW11; and SW12, SW13, SW14, and SW15, respectively. Columns 1,2,3 and 4 include SW0, SW4, SW8 and SW12; SW1, SW5, SW9 and SW13; SW2, SW6, SW10 and SW14; and SW3, SW7, SW11, and SW15, respectively. For each column there is a corresponding resistor R having a value of approximately 4.7k ohms. Each switch has a contact A and contact B. In each row all contacts A are connected together and in each column, all contacts B are connected to one side of the resistor R associated with the column. The other side of each resistor R is connected to a +five (5) volt d.c. source. Contacts A of SW0, SW4, SW8 and SW12 are also connected to an output terminal of a latch L1 and a line R1; an output terminal of a latch L2 and a line R2; an output terminal of a latch L3 and a line R3; and an output terminal of a latch L4 and a line R4, respectively. Lines W1, W2, W3 and W4, which are connected to CPU 38, are also connected to input terminals of latches L1, L2, L3 and L4, respectively. Lines R5, R6, R7 and R8 are connected to CPU 38 and are also connected to contacts B of SW12, SW13, SW14 and SW15, respectively.

Referring now to FIGS. 4A and 4B, operation of data entry system 30 is as follows: When power is initially supplied to data entry system 30, CPU 38 will supply a digital signal based on instructions from ROM 39 to display 34 which will result in the words WAIT and then READY appearing in the window of the latter. The processor 38 is now in a routine, hereinafter referred to as the READY ROUTINE, which will periodically check a "busy" line (to be discussed below) and call a SCAN routine to determine which key, if any, has been depressed.

The SCAN routine will direct CPU 38 to write up to four different four bit signals, that is, four different nibbles into switching network 37 through latches L1, L2, L3 and L4. The writing of these nibbles by CPU 38 is based on instructions from ROM 39 in order to determine whether one of the plurality of keys 35 has been depressed. Such writing is also referred to as scanning network 37. The SCAN routine encompasses a number of steps as will be discussed below and will always, as the last step in its routine, return program control to whichever previous routine called it.

Initially, the SCAN routine directs the writing of one or more nibbles into switching network 37 as follows: A first nibble of digital information is written into latches L1–L4 on lines W1–W4, respectively, wherein each bit of the nibble is written into a different one of the four latches. For exaple, a 0111 nibble means that a 0 bit is written into L1 on line W1 and 1 bit is written into L2–L4 on lines W2–W4, respectively. The nibble is then supplied to contacts A of column 1. In response to the nibble, network 37 generates a byte, that is, eight (8) bits of digital information which are read from network 37 by CPU 38 on lines R1–R8. Assuming a byte is defined by b1, b2, b3, b4, b5, b6, b7, b8, wherein b1–b8 are bits, then bits b1–b8 correspond to lines R1–R8, respectively. Furthermore inasmuch as lines R1–R4 are connected to the output terminals of latches L1–L4, whatever logic level is stored in latches L1–L4 will appear on lines R1–R4, respectively. In other words, whatever nibble is written into the latches will appear as bits b1–b4 of the byte read from network 37.

1 and 0 bits are actually +5 and 0 volts, respectively. Therefore, whenever a 0 bit is applied to contact A of a switch which has been closed, contact B will be at 0 volts. Correspondingly, whenever a 1 bit is applied to contact A of a switch htat has been closed, contact B will be at +5 volts. However, when a switch is not closed, contact B will always be at +5 volts even when a 0 bit is applied to contact A assuming no other contact B in that column is at zero volts. That is, since all contacts B in any column are connected together, if any of them are at 0 volts, then all contacts B in that column are at 0 volts. Furthermore, if none of the keys have been depressed, then contacts B of all switches will be +5 volts (i.e. 1 bit). Accordingly, if no key has been depressed a byte of 01111111 will be read by CPU 38 in response to a nibble of 0111 written into network 37 through latches L1–L4. Assuming none of the keys 36 have been depressed yet, the CPU will subsequently and sequentially write nibbles of 1011, 1101 and 1110 into network 37 through latches L1–L4. All contacts B will remain at +5 volts while network 37 is scanned. Therefore, the bytes read by CPU 38 will be 10111111, 11011111 and 11101111, respectively.

If, however, a key associated with, for example, SW3 is depressed such that SW3 is closed, a nibble of 0111 written into network 37 will produce 0 volts at contact B of SW3 since all A contacts of rows 1 are at 0 volts. All other contacts B in row 1, however, will be at +5 volts. Accordingly, the byte read by CPU 38 from network 37 will be 01111110. Furthermore, for nibbles of 1011, 1101 or 1110 when SW3 is depressed, the bytes generated by network 37 would be 10111111, 11011111 and 11101111, respectively.

In otherwords, nibble 0111 effectively enables row 1 such that depression of SW0, SW1, SW2 or SW3 will result in a 0 bit appearing on lines R5, R6, R7 or R8, respectively. Similarly, nibble 1011 enables row 2 such that depression of SW4, SW5, SW6 or SW7 will result in a 0 bit appearing on lines R5, R6, R7 or R8, respectively. Nibbles 1101 and 1110 enable rows 3 and 4, respectively, such that depression of SW8, SW9, SW10 or SW11 for nibble 1101 and depression of SW12, SW13, SW14 or SW15 for nibble 1110 will produce a 0 bit in lines R5, R6, R7 or R8, respectively. That is, each nibble corresponds to enabling a particular row and lines R5–R8 are used to indicate a particular column having a depressed key. Thus any key may be identified as having been depressed since the row enabled is known and the column having the depressed key is detected by CPU 38.

As is readily apparent, in order to scan all sixteen switches only four different nibbles are required. Of course, based on the first, second or third nibbles read into network 37, a key may be identified as having been depressed. Once a key has been identified as having been depressed, no further nibbles will be written into network 37. Therefore, not all four nibbles will always be written into network 37.

Each byte read by CPU 38 is written into an accumulator 42 of CPU 38 and thereafter stored in one of eight registers designated as R0–R7 within RAM 41. The register in which the byte is stored will hereinafter be referred to as the storage register. Based on instructions from ROM 39, CPU 38 instructs one of the eight registers to act as counter. CPU 38 looks at bits b5–b8 of each byte stored in the storage register to determine if a 0 bit is present. At the same time, the counter is initialized at a value of zero when nibble 0111 is written into network 37. If bit b5 of the byte read from network 37 in response to nibble 0111 is a 1, the counter is incremented by one from a value of zero to one. Bit b6 is then checked by CPU 38 to see if it is 0. If it is 1, the counter is incremented by 1 again. Bit b7 is then checked and if a 1 appears then bit b8 is checked, each time incrementing the counter by one if a 1 bit appears. If b8 is 1, then a nibble 1011 is written into network 37. The above pattern of checking bits b5–b8 is repeated; incrementing the counter by one each time a 1 bit appears. Nibble 1101 will then be written into network 37. If no 1 bits appear in b5–b8 in response to nibble 1101, nibble 1110 is written into network 37.

If no 0 bit is detected in response to writing in the four different nibbles, ROM 39 instructs CPU 38 to place the value of 255 (FF in hexadecimal notation) in accumulator 42. If, however, in response to writing in any of the four different nibbles a 0 bit is detected, no further increments in the counter will occur. The value of the counter is added to a base reference value supplied by ROM 39 in accumulator 42. The new value stored in accumulator 42 corresponds to one of the sixteen keys of membrane switch 32. Regardless of the value placed in accumulator 42, the SCAN routine is now complete. Accordingly, program control will return to the READY routine.

If no key has been depressed, the READY routine will see the value of 255 in accumulator 42 and in response thereto will call the SCAN routine once again. The steps of calling the SCAN routine, returning to the READY routine and recalling the SCAN routine will continue until depression of a key is detected. If, however, a key has been depressed the value in accumulator 42 is used as an index into a table stored in ROM 39 to fetch a beginning address of a FUNCTION routine also stored in ROM 39. Fetching of an address is required only for purposes of executing a FUNCTION routine. CPU 38 executes the FUNCTION routine beginning at this address.

Several of the FUNCTION routines such as temperature, blood pressure, etc. require additional information, that is, numerical data and symbols, such as a plus (+) or a minus (−) sign, decimal point, slash and arrows, to be entered into system 30. However, prior to entering such additional information, data and symbol instructing signals, known as flags, which are used to identify subsequent communications to system 30, are sent from ROM 39 to RAM 41 by CPU 38. Without such flags, it would not be possible to determine how the next byte or bytes supplied by switching network 37 should be processed. There are ten flags stored in RAM 41 for each function, such as oxytocin, which requires data and/or symbols to be communicated as the next entry to system 30. The flags will indicate whether to identify the next entry or entries as an arrow or plus (+) or minus (−) sign, whether to accept a decimal point (.) or slash (/) as an appropriate next entry, the starting position of the data displayed in window 34a, the maximum number of digits of data to be associated with any particular function, the maximum number of digits permitted to the left of a decimal point, the number of characters placed in a buffer 41b which are to be transmitted to recorder 20, the response of CPU 38 to a clear function, clear data or enter command, how many digits of data have been entered by a user of system 30, if a decimal point has been entered, and if a zero can be the first entry of numerical data. Based on these flags, depression of a key which is inconsistent with a previously communicated function will not be accepted by CPU 38 for display in window 34a or storage in buffers 41a and 41b of RAM 41. That is, communication of data which is inconsistent with a previously communicated function will be ignored by processor 33. Thus, for the oxytocin routine flags are set up to expect an arrow, which is indicative of an increase or decrease in the oxytocin rate, as an appropriate next entry to system 30. With respect to further additional entries, other flags are set up the oxytocin routine which include acceptance of a decimal point as an entry and permitting a maximum of 3 digits of data and a maximum of two digits of data to the left of the decimal point. Other flags for the oxytocin routine are set up as the data and symbols are entered. Accordingly, when key 35b is depressed following depression of key 35a. CPU 38 will identify the depressed key as an arrow (↑) indicating an increase in the oxytocin rate rather than the function $O_2$ or a plus (+) sign which are also associated with depression of key 35b.

Detection of depressed keys once in a FUNCTION routine is as follows: The FUNCTION routine will set up various flags if required and then call the SCAN routine in order to identify subsequent key depression. Each time the SCAN routine is called, the value in accumulator 42 at the completion of the SCAN routine is used by the FUNCTION routine to determine if a key has been depressed. More particularly, if no key has been depressed the SCAN routine is recalled. The above pattern of calling the SCAN routine, returning to the FUNCTION routine and recalling the SCAN routine is repeated until depression of a key is detected or the maximum period of time between communications is exceeded as discussed below. If a key has been depressed within the predetermined time period, the accumulator value is processed as either numerical data, a symbol or a clear function, clear data or enter command (to be discussed below) in accordance with the flags.

As an example of a complete communication, consider communicating an increase in the oxytocin rate of 8.5 milliunits/min. Initially key 35a is depressed which places the corresponding switch underlying key 35a in a conductive state. In response to CPU 38 scanning switching network 37, the oxytocin key is identified as having been depressed based on the value in the counter and an oxytocin routine is executed from ROM 39 by CPU 38. The oxytocin routine will direct storage of flags in RAM 41. Additionally, the oxytocin routine will direct CPU 38 to store a display signal representative of the word oxytocin in a buffer 41a of RAM 41. Prior to the next entry in the communication, the display signal is supplied to display device 34. Device 34 will process the display signal such that the word oxytocin will appear in the liquid crystal display window 34a. Sequential depression of keys 35b, 35h, 35and 35j will result in display signals representative of the up arrow (↑), the number eight (8), the decimal point (.) and the number five (5) being initially stored in buffer 41a and then displayed in device 34. A second buffer 41b of RAM 41 is used to store a message signal supplied by ROM 39 which comprises the identified function (oxytocin) and, if required, associated data (↑ 8.5) for subsequent transmission to fetal monitoring device 21. Such transmission, however, will not occur until key 35d designated as the "mark/enter" key is depressed. Depression of key 35d following a message, such as oxytocin ↑ 8.5, is referred to as the enter command and indicates to CPU 38 that the user has completed his communication and that the communication can now be transferred to fetal monitoring device 21 for recordation on strip chart 10 by recorder 20. Following depression of key 35d, the READY routine will be called up by CPU 38 resulting in the word READY reappearing in window 34a and thereby notifying the user that the system is ready to accept the next function entry and, if appropriate, associated numerical data and symbols.

System 30 also provides keys 35e and 35f which represent the clear function and clear data commands, respectively. In response to identification that the clear function key 35e has been depressed. ROM 39 will instruct CPU 38 to clear, that is, erase all information displayed on display window 34a and return program control to the READY routine without sending data to device 21. Similarly, in response to depression of the clear data key 35f, any data displayed in window 34a will be cleared and program control will be returned to the start of the FUNCTION routine.

As previously mentioned there are 16 functions to choose from, however, only thirteen functions including BP, VE, POS CHG, TEMP, ROM, OXYTOCIN, PULSE, pH, IV, RESP, FM, $O_2$ and MED are shown on the face of membrane switch 32. In order to choose from the other three functions, depression of key 35g, designated as VE, will result in selection and display of the effacement function (EFF %). If mark/enter key 35d is now depressed, the message signal associated with the function VE will be transmitted to recorder 20. Subsequent depression of key 35e rather than key 35d will change the selected and displayed function from effacement to dilation (DIL). Another depression of key 35e will switch the selected and displayed function from dilation to station (STA). Thus sixteen functions of medical information are possible in this preferred embodiment of the present invention.

As also previously indicated, conductor 31 includes a number of separate lines such as a line for providing power from fetal monitoring device 21 to data entry system 30. Conductor 31 also includes a "strobe" line used to inform recorder 20 that a byte of the information stored in buffer 41b of RAM 41 has been sent to recorder 20, an "input buffer full" (IBF) line to indicate to CPU 38 that the recorder is ready to accept the next byte of information stored in buffer 41b, a "busy" line to indicate that the recorder is unable to accept any further information from buffer 41b and an "event marker" line (to be described below).

Recorder 20 is able to accept three functions for printing at one time and a fourth function which is stored in a buffer of recorder 20 (now shown). Until the information stored in the buffer of recorder 20 is removed therefrom for printing by recorder 20, the busy line will transmit a signal from recorder 20 to CPU 38 to indicate no further information communicated to system 30, except an "event marker" (to be discussed below), will be accepted. In response to this transmitted signal by the busy line, the word WAIT will appear in window 34a. Once the information stored in the buffer of recorder 20 has been removed therefrom for printing by recorder 20, a message READY, produced by the READY routine, will reappear in display window 34a to indicate to the user that the system 30 is now ready to accept further communications thereto. As previously noted, the word WAIT will also appear in display 34a initially as system 30 is turned on until the READY routine has been processed by CPU 38.

System 30 is also able to supply an event marker signal to recorder 20. In response to receiving the event marker signal, an arrow 50, as shown in FIG. 2, is printed by recorder 20. In communicating that an event marker is to be printed by recorder 20 on strip chart 10, mark/enter key 35d is depressed once the READY message appears in window 34a. The byte generated by switching network 37 in response to depression of key 35d is read by CPU 38 and subsequently identified by the latter as requesting that a event marker be printed. An event marker routine similar to other function routines will be processed by CPU 38 resulting in the words EVENT MARK being displayed in window 34a and in the event marker signal, which is stored in ROM 39, being sent on the event marker line to recorder 20 for printing of arrow 50.

Data entry system 30 also has a timing routine which clocks the period of time between communications to data entry system 30. If the length of time between communications exceeds a predetermined maximum period of time, as controlled by a clock within CPU 38 (not shown), the clear function routine will be called upon by CPU 38 such that the previous communication will be erased from display window 34a and program control will be returned to the READY routine. More specifically, a counter within CPU 38, not shown, which forms part of the clock, counts the length of time between communications to switching membrane 32 and based on instructions from ROM 39 will cause display window 34a to erase the contents therein and return program control to the READY routine if the time duration exceeds a predetermined period.

It should be noted that display window 34a can accommodate a maximum of sixteen characters and that buffer 41a has sixteen locations, each location being a byte in length and corresponding to a character in display window 34a. Furthermore, buffer 41b has a maximum length of ten bytes wherein the first byte represents the function communicated to membrane switch 32. If the message supplied by buffer 41b to recorder 20 contains in the first byte a signal having a code of one (1) to sixteen (16), representing the sixteen functions which can be communicated to switching membrane 32, recorder 20 will accept this first byte. However, if the code is greater than sixteen (16) then recorder 20 will instruct CPU 38 that an error has occurred. More particularly, an error message will be displayed in window 34a as ERROR 1 indicative of an invalid code transmitted to recorder 20. Other errors which will be displayed in window 34a, designated as ERROR 2 and ERROR 3 indicate that an internal error check by CPU 38 is unable to both write and read into RAM 41 and that there is a problem in the transmission link between CPU 38 and recorder 20, respectively.

It now will be readily appreciated from the foregoing that the present invention provides a new and improved method [of] *and apparatus for* communicating medical information to a recorder for printing on a strip chart. More particularly, the present invention avoids the need for recording by hand pertinent medical information which is normally required in order to accurately interpret the fetal heart rate determined by device 21. Furthermore, the present invention provides the user of system 30 the freedom to select when and which functions are to be recorded on strip chart 10 by recorder 20.

Having specifically described an illustrative embodiment of the invention with reference to the accompanying drawings, it is to be understood that the invention is not limited to this precise embodiment and that various changes and modifications may be effected therein by one skilled in the art without departing from the scope and spirit of the invention as defined in the appended claims.

We claim:

1. [For] *In a fetal monitoring device including* printing by a strip chart recorder and displaying by a display device medical information, a method comprising:

communicating said medical information to switching membrane means *in a remote control device while held in the hand of a user located remote from said recorder and display device;* scanning said switching membrane means;

generating one of a plurality of membrane signals in response to each communication and scan;

identifying said one of said plurality of membrane signals;

displaying by said display device said medical information in response to said identification; and

*either* printing by said recorder said medical information in response to said identification *or cancelling said medical information in favor of communicating either corrective or new medical information to said switching membrane means, after said medical information has been displayed.*

2. A method of printing and displaying medical information as in claim 1; wherein said switching membrane means comprise a plurality of depressable keys overlying a corresponding plurality of switches and wherein said communicating of said medical information comprises depressing at least one of said plurality of keys so that said corresponding switch is switched to its conductive state.

3. A method of printing and displaying medical information as in claim 2; wherein each of said plurality of membrane signals comprises digital information.

4. A method of printing and displaying medical information as in claim 3, wherein said identifying comprises reading said one of said plurality of membrane signals, counting the number of non-zero bits of information read, fetching a reference value stored in a first memory device and adding the number of said non-zero bits counted to said reference value to produce an accumulator value.

5. A method of printing and displaying medical information as in claim 4; further comprising determining completion of said communication of medical information prior to printing any portion of said medical information.

6. A method of printing and displaying medical information as in claim 5; further comprising storing a display signal and a message signal supplied by said first memory device in a second memory device in response to said accumulator value.

7. A method of printing and displaying medical information as in claim 6; wherein said displaying of said medical information is in response to said display device receiving said display signal and further wherein said printing of said medical information is in response to said recorder receiving said message signal.

8. A method of printing and displaying medical information as in claim 7; wherein said medical information is associated with fetal heart rate and uterine activity.

9. A method of printing and displaying medical information as in claim 8; wherein said medical information is selected from the group of functions consisting of ph, temperature, intravenous rate, oxygen rate, pulse, respiration, blood pressure, oxytocin rate, effacement, dilation, station of fetus, maternal position change, rupture of membrane, medication, fetal movement and vaginal exam.

10. A method of printing and displaying medical information as in claim 9, wherein initial depression of one of said plurality of keys communicates one of said group of functions to said switching membrane means and subsequent depressions of said plurality of keys communicates numerical data and symbols associated with the communicated function.

11. A method of printing and displaying medical information as in claim 10; wherein identifying of one of said plurality of membrane signals generated in response to said initial depression further comprises fetching an address stored in said first memory device in accordance with said accumulator value and executing a routine beginning at said address representative of said communicated function.

12. A method of printing and displaying medical information as in claim 11; further comprising storing a plurality of flag signals in said second memory device in response to said initial depression of said switching membrane means whereby identifying one of said plurality of membrane signals generated by said subsequent depressions is in response to said plurality of flag signals.

13. A method of printing and displaying medical information as in claim 12; wherein said first memory device is a ROM and said second memory device is a RAM.

14. A method of printing and displaying medical information as in claim 13; wherein said display device includes a liquid crystal display for displaying said medical information.

*15. In a fetal monitoring device including printing by a strip chart recorder and displaying by a display device medical information, a method comprising:*

*communicating said medical information to switching means in a hand-held remote control device located remote from the recorder and display device;*

*scanning said switching means;*

*generating one of a plurality of signals in response to each communication and scan;*

*identifying said one of said plurality of signals;*

*displaying by said display device said medical information in response to said identification; and*

*either printing by said recorder said medical information in response to said identification, or cancelling said medical information in favor of communicating either corrective or new medical information to said switching means, after said medical information has been displayed.*

*16. A method of printing and displaying medical information as in claim 15; wherein said switching means comprises a plurality of depressible keys overlying a corresponding plurality of switches and wherein said communicating of said medical information comprises depressing at least one of said plurality of keys so that said corresponding switch is switched to its conductive state.*

*17. A method of printing and displaying medical information as in claim 16, wherein each of said plurality of signals comprises digital information.*

*18. A method of printing and displaying medical information as in claim 17, wherein said identifying comprises reading said one of said plurality of signals, counting the number of non-zero bits of information read, fetching a reference value stored in a first memory device, and adding the number of said non-zero bits counted to said reference value to produce an accumulator value.*

*19. A method of printing and displaying medical information as in claim 18, further comprising determining completion of said communication of medical information prior to printing any portion of said medical information.*

*20. A method of printing and displaying medical information as in claim 19, further comprising storing a display signal and a message signal supplied by said first memory device in a second memory device in response to said accumulator value.*

*21. A method of printing and displaying medical information as in claim 20, wherein said displaying of said medical information is in response to said display device receiving said display signal and further wherein said printing of said medical information is in response to said recorder receiving said message signal.*

*22. A method of printing and displaying medical information as in claim 21, wherein said medical information is associated with fetal heart rate and uterine activity.*

*23. A method of printing and displaying medical information as in claim 22, wherein said medical information is selected from the group of functions consisting of ph, temperature, intravenous rate, oxygen rate, pulse, respiration, blood pressure, oxytocin rate, effacement, dilation, station of fetus, maternal position change, rupture of membrane, medication, fetal movement and vaginal exam.*

*24. A method of printing and displayig medical information as in claim 23, wherein initial depression of one of said plurality of keys communicates one of said group of functions to said switching means, and subsequent depressions of said plurality of keys communicates numerical data and symbols associated with the communicated function.*

*25. A method of printing and displaying medical information as in claim 24, wherein identifying of one of said plurality of signals generated in response to said initial depression further comprises fetching an address stored in said first memory device in accordance with said accumulator value and executing a routine beginning at said address representative of said communicated function.*

*26. A method of printing and displaying medical information as in claim 25, further comprising storing a plurality of flag signals in said second memory device in response to said initial depression of said switching means, whereby identifying one of said plurality of signals generated by said subsequent depressions is in response to said plurality of flag signals.*

*27. A method of printing and displaying medical information as in claim 26, wherein said first memory device is a ROM and said second memory device is a RAM.*

*28. A method of printing and displaying medical information as in claim 27, wherein said display device includes a liquid crystal display for displaying said medical information.*

*29. For use with fetal monitoring apparatus wherein medical data is recorded on a continuous charge by a strip chart recorder, a hand-held remote control device for enabling an operator at a location remote from said strip chart recorder to record selectively information related to said medical data at preselected locations on the strip chart, said device comprising:*

*key pad means for enabling the operator to select the information to be recorded on said chart;*

*processing means responsive to actuation of said key pad means by said operator for producing information signals representative of said selected information;*

*display means responsive to said information signals for displaying said selected information for verification prior to printing; and*

*means adapted to be coupled to said strip chart recorder for selectively causing the displayed information to be recorded on said strip chart in a preselected location relative to said recorded medical data.*

*30. The device of claim 29, wherein said key pad means includes:*

*a plurality of keys each actuable and designated to represent a portion of said information for display and recording; and*

*a plurality of switching means responsive to selective actuation of said plurality of keys, respectively, for coupling said information into said processing means.*

*31. The device of claim 30, wherein said processing means includes:*

*means for scanning said plurality of switching means and for producing said information signals dependent upon the particular combination of conductive and non-conductive ones of said plurality of switching means as a result of either selective actuation or successive actuation of either a particular one or ones of said keys; and*

*storage means for storing said information signals.*

*32. The device of claim 31, wherein said means for selectively causing the displayed information to be recorded on said strip chart further includes means responsive to depression of an "entry key" of said key pad means for enabling the former.*

*33. The method of claim 15, further including in said printing step the printing of said medical information only in areas of a strip chart recording material free of curves being recorded for fetal heartbeat and uterine activity.*

* * * * *